United States Patent [19]

Magoon et al.

[11] 4,312,347
[45] Jan. 26, 1982

[54] POSITIVE PRESSURE DRUG RELEASING DEVICE

[75] Inventors: Keith E. Magoon; Lawrence E. Evans; Frederick B. Hembrough, all of Ames, Iowa

[73] Assignee: Iowa State University Research Foundation, Inc., Ames, Iowa

[21] Appl. No.: 124,542

[22] Filed: Feb. 25, 1980

[51] Int. Cl.³ .............................................. A61M 7/00
[52] U.S. Cl. ..................................................... 128/260
[58] Field of Search ................. 128/260, 261, 172, 769

[56] References Cited

U.S. PATENT DOCUMENTS

| | | |
|---|---|---|
| 1,476,946 | 12/1923 | Bessesen . |
| 3,057,344 | 10/1962 | Abella et al. ........................ 128/769 |
| 3,492,993 | 2/1970 | Tillman ................................. 128/261 |
| 3,659,600 | 5/1972 | Merrili ................................. 128/172 |
| 3,788,322 | 1/1974 | Michaels .............................. 128/260 |
| 3,929,132 | 12/1975 | Higuchi ............................... 128/260 |
| 3,948,263 | 4/1976 | Drake .................................. 128/260 |
| 4,004,582 | 1/1977 | Nakamura et al. ................. 128/260 |
| 4,014,334 | 3/1977 | Theeuwes ........................... 128/260 |
| 4,036,227 | 7/1977 | Zaffaroni ............................ 128/260 |
| 4,160,452 | 1/1979 | Theeuwes ........................... 128/260 |

Primary Examiner—C. Fred Rosenbaum
Attorney, Agent, or Firm—Tilton, Fallon Lungmus

[57] ABSTRACT

A positive pressure long-term drug delivery device particularly useful for the intravaginal or intrauterine release of a drug capable of passing through a diffusion membrane and being absorbed by the vaginal or uterine epithelium. The device includes a tubular casing having a plunger urged by a compression spring to create a continuous positive pressure on a drug in liquid form within the chamber of the casing, a supported membrane at one end of the casing through which such drug diffuses at a predetermined rate, and resilient elements at the opposite end of the casing for facilitating retention of the device throughout the term of administration of the drug.

9 Claims, 4 Drawing Figures

U.S. Patent   Jan. 26, 1982   4,312,347
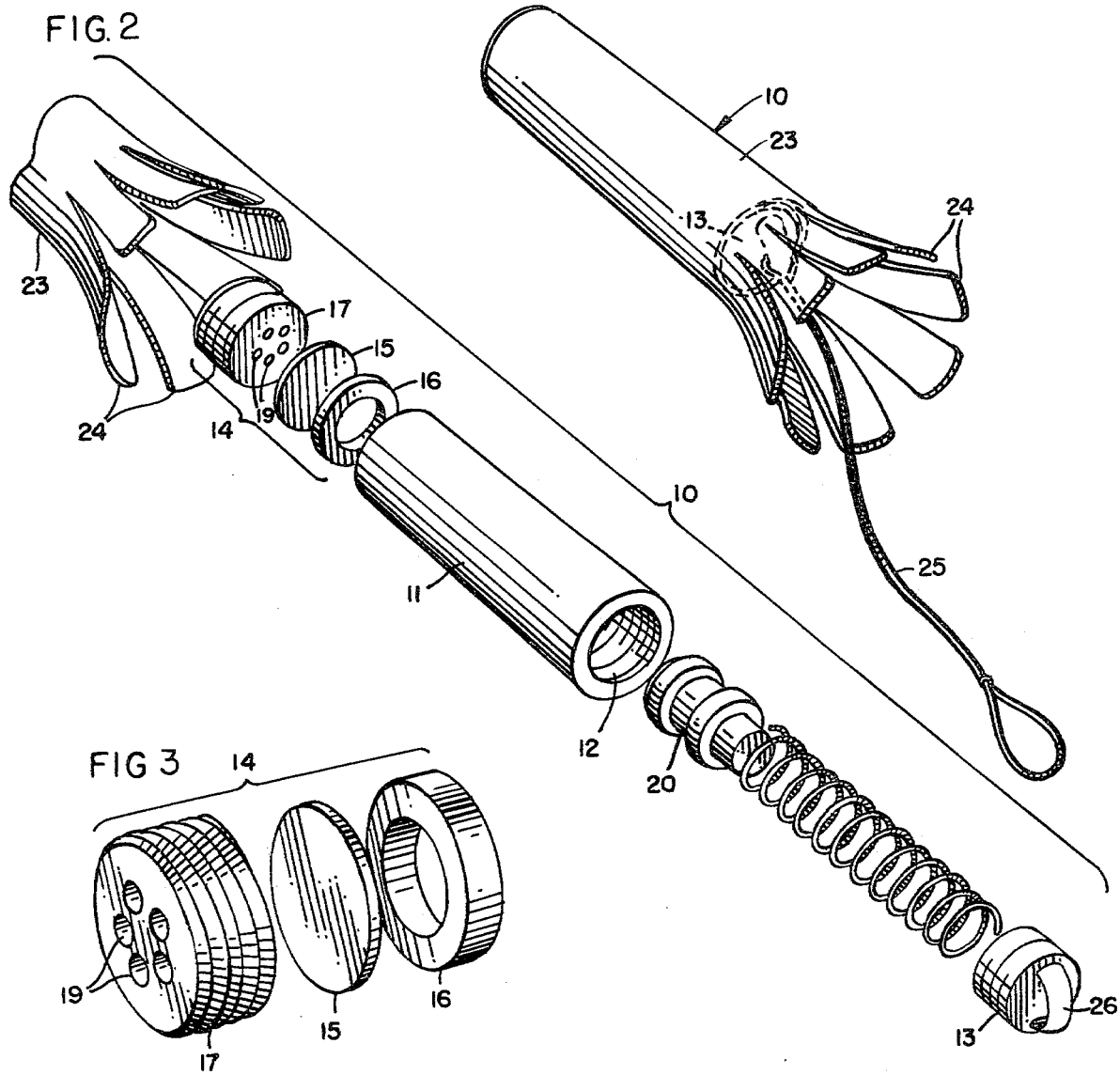
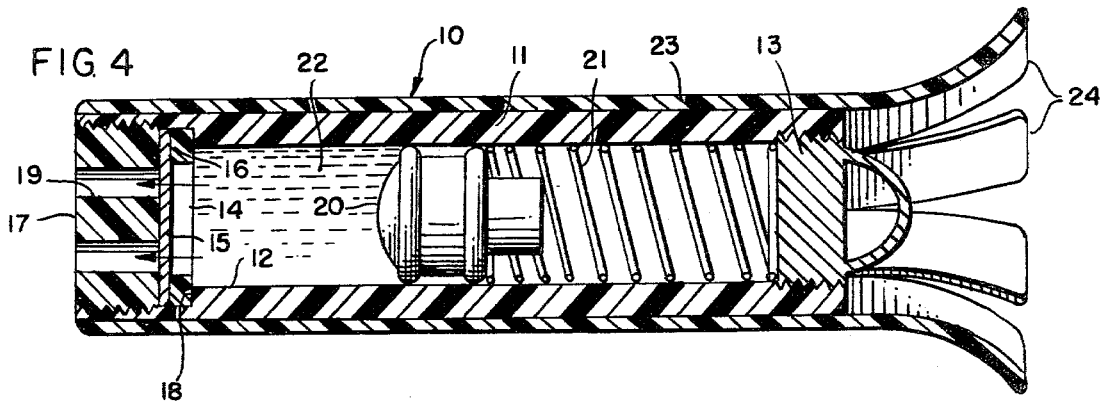

POSITIVE PRESSURE DRUG RELEASING DEVICE

BACKGROUND AND SUMMARY

While the device of this invention is applicable for the long-term delivery of various drugs to a wide variety of animals, not excluding human beings, it is believed particularly useful for treating domestic animals for the purpose of reversibly controlling reproduction. The need is particularly acute with regard to control of the canine population in view of the increasing number of unwanted stray and abandoned dogs in this country and elsewhere. Such free-roaming animals have been known to cause property damage and attack other animals (including man) as well as carrying and spreading diseases. Few methods are presently available for successfully controlling canine reproduction.

Ovariohysterectomy (spaying) constitutes a positive method of reproduction control; however, ovariohysterectomy has met with opposition because of its irreversibility (especially with respect to pets) and because of its cost (primarily with respect to stray or abandoned animals). As an alternative to spaying, mechanical devices have recently become available which are designed to prevent penile insertion into the female but, unfortunately, such devices are of limited effectiveness.

Chemosterilants have been studied and found to control fertility, but they often cause pathological changes in the uterus making ovariohysterectomy necessary. All known exogenous progestens cause cystic endometrial hyperplasia, endometritis, and mucometra. Of various progestens that have been studied, only magestrol acetate is approved for commercial use and, in addition to the disadvantages already mentioned, is relatively expensive.

The problems with chemosterilants is not only one of drug selection but also of ease and effectiveness of administration. Thus, subcutaneous androgen implants such as testosterone have been tested in the bitch and found to inhibit estrus with minimum side effects. Implantation is, however, a surgical procedure usually requiring the administration of anesthesia and, depending on the weight of the animal, more than one implant may be necessary. Oral administration, although simpler, is time-consuming and inconvenient since estrus is inhibited only for the duration of a daily dosage which must be initiated prior to the beginning of proestrus to be effective.

Osmotic devices for delivering drugs in various selected environments have been disclosed, for example, in U.S. Pat. Nos. 4,160,452, 4,036,227, and 4,014,334. While such devices are intended to deliver drugs at continuous and predetermined rates for extended periods, their effectiveness depends on osmotic pressure which in turn depends on factors which may be variable. The presence and extent of fluid surrounding such devices, and the precise nature of such fluid, all affect the operation of osmotic devices.

Other patents indicating the state of the art are U.S. Pat. Nos. 3,659,600, 3,984,263, 3,492,993, 1,476,946, and 3,929,132, and the references cited therein.

In view of the above, it is a main object of this invention to provide a long-term drug delivery device suitable for intrauterine or intravaginal (preferably the latter) placement, which is positive-acting in its operation. Specifically, it is an object to provide an intravaginal or intrauterine device which utilizes a positive pressure mechanism for the gradual and continuous delivery of a drug to a warm-blooded animal.

The positive pressure mechanism includes a compression spring which exerts a constant force to reduce the size of a variable-volume chamber containing a drug solution which is capable of passing through a diffusion membrane and of being absorbed by the vaginal or uterine epithelium. One wall of the chamber includes a supported diffusion membrane; a second wall of the chamber, or a compartment of that chamber, takes the form of a plunger driven by the compression spring. The casing defining the chamber is preferably of cylindrical shape and is dimensioned to be received within the body cavity of the animal to be treated. Where the cavity constitutes the vaginal cavity, the device is additionally provided with flexible retaining elements which project radially outwardly from the end of the casing opposite from the end in which the diffusion membrane is supported. The result is a dependable and relatively simple drug-delivery device which utilizes a positive-pressure mechanism, not dependent upon osmotic pressure, and which is particularly suitable for delivering estrus-controlling drugs to livestock, pets, and other warm-blooded animals.

Other features, objects, and advantages of the invention will become apparent from the drawings and specification.

DRAWINGS

FIG. 1 is a perspective view of a device embodying this invention.

FIG. 2 is an exploded fragmentary perspective view depicting the various components of the device.

FIG. 3 is an enlarged exploded perspective view illustrating the diffusion membrane and its supporting elements.

FIG. 4 is an enlarged longitudinal sectional view of the device illustrating the operative relationship of parts.

DETAILED DESCRIPTION

Referring to the drawings, the numeral 10 generally designates a drug releasing device or capsule having a tubular casing 11 defining a cylindrical chamber 12. One end of the chamber is closed by a threaded plug or end wall 13, the inner surface of the chamber being threaded to receive the plug. The opposite end of the casing is open and receives a supported diffusion membrane assembly 14 (FIG. 3). The assembly 14 includes a diffusion membrane 15, a retaining ring 16, and an apertured membrane support member 17. As shown most clearly in FIG. 4, the casing 11 is counterbored to provide a shoulder 18 for bracing the retaining ring 16. The membrane 15 is sandwiched between the ring and the apertured support member 17, the latter being threadedly received within the delivery end of the casing. The exposed area of the diffusion membrane 15, and hence the diffusion of drug through that membrane, may be varied by selecting a ring 16 having a central opening of the desired size.

The membrane support member is provided with a plurality of apertures 19 which are parallel with the axis of that member and extend completely therethrough. While such apertures may perform a secondary function is providing a means for gripping the member with a suitable wrenching device in order to screw it tightly into place, the primary function of such apertures is to provide discharge passages for the delivery of a treatment medium to the host animal. Five such apertures are shown in the drawings although the number and size of such apertures should not be taken as critical. In the delivery of a drug, the metering function is performed primarily by the diffusion membrane; hence, the number and total area of the apertures should not be so small as to interfere with the metering action of the diffusion membrane, nor should they be so large or few in number that the member 17 fails to provide adequate support for the membrane. Within such general guidelines, the number and size of the apertures 19 may be varied considerably.

Within chamber 12 is a plunger 20 which slidably and sealingly engages the cylindrical inner surface of the casing. A compression spring 21 is interposed between end wall 13 and plunger 20 to provide a constant and generally uniform force urging the plunger towards the delivery end of the device.

Within the chamber 12, in the space between plunger 20 and the diffusion membrane 15, is a drug solution 22. The liquid treatment agent may be any of a variety of drug solutions capable of diffusing through membrane 15 and being absorbed by the uterine or vaginal epithelium. The device of this invention is considered particularly useful for the long-term administration of an estrus inhibiting drug such as, for example, mibolerone (7 alpha, 17-dimethyl-19nortestosterone), and androgenic anabolic steroid; however, the device may be used for administering other chemosterilants (such as magestrol acetate, chlormadinone, melengestrol acetate, delmadinone acetate, noresthisterone acetate, testosterone, etc.) as well as steroids and other medicaments for treatment of arthritis, hormones for correcting hormonal imbalances (insulin), antibiotics, and the like. With respect to the operation of the device, the essential factors are that the drug be stable throughout the term of administration and be capable of diffusing through membrane 15 and being absorbed through the wall of the body cavity.

For vaginal implantation the device is provided with a resilient sleeve 23 (silicone rubber) which covers the side wall of the casing and which is provided at the proximal end of the device (the end opposite the delivery or distal end) with a multiplicity of flexible fingers 24. The fingers 24 extend axially beyond end wall 13 and flare radially outwardly. It has been found that the spring action of the outwardly flared integral fingers 24 is highly effective as retaining means for holding the device within the vaginal cavity. The fingers flex outwardly for gently but effectively engaging the vaginal epithelium to secure the device in operative position. To facilitate removal of the device, an extraction cord 25 may if desired be secured to the end wall 13 of the casing. As shown in FIGS. 1, 2, 4, the plug or end wall is provided with an integral loop or ring 26 for attachment of the extraction cord or other removal device.

The materials from which the device is formed may vary considerably, the main requirement being that they be durable, function properly, and be non-toxic and non-irritating. The cylindrical portion of the casing 11 may, for example, be stainless steel although polymeric materials such as polytetrafluoroethylene may be used. Similarly, the retaining ring 16, membrane support member 17 and end plug 13 may be formed of a durable inert plastic (as shown) or of a metal having similar non-reactive properties. Membrane 15 may be formed of any suitable polymeric material capable of functioning as a diffusion membrane; silicone rubber, preferably reinforced medical grade silicone rubber subdermal implant material sold under the designation Silastic Sheeting 501-7 by Dow Chemical Company, Midland, Michigan, has been found effective but other known membrane materials may be used. Silicone rubber is also a suitable material for the fabrication of outer sleeve 23 with its integral spring fingers 24 but, again, other polymeric materials having similar properties may be selected.

The rate of delivery of the drug is controlled primarily by the concentration of the drug solution but may also be adjusted to varying the thickness and exposed area of the membrane and the pressure developed by the compression spring, such delivery rate being selected on the basis of the dosage requirements for the particular treatment or effect sought to be achieved. The spring 21 should exert a substantially constant force through the full range of movement of plunger 20. In general, that force should develop a pressure upon fluid 22 within the range of about 400 to 1500 mm Hg, preferably 600 to 1200 mm Hg. The effect is to overcome or make negligible the back diffusion osmotic pressures external to the membrane, assist in maintaining a relatively constant concentration within the device, and contribute to providing a substantially constant flow across the membrane. The effect is revealed by the following formula:

$$N_i = C_i K \Delta p + D(\Delta C_i / im \Delta Z)$$

where N is the net flow of drug solution i across the diffusion membrane, C is the concentration of the drug solution, K is the permeability of the membrane, $\Delta p$ is the difference in pressure (i.e., the positive pressure generated by the spring plus osmotic pressure from the inside of the membrane, to the osmotic pressure (back diffusion) from the outside of the membrane), $D_{im}$ is the diffusion coefficient across the membrane, and $\Delta Z$ is the change in distance across the membrane. Thus, it is evident that the flux of a species across the membrane, in this case the drug solution, is the sum of a flux driven by pressure and a flux driven by concentration. Stated differently, an increase or reduction in the pressure created by selecting springs of different strength produces a generally proportional increase or decrease in the flow across the membrane, other factors remaining constant. Since the helical compression spring exerts a substantially constant force and therefore creates a substantially constant linear pressure, the result, using any such spring capable of producing a constant internal pressure substantially greater than back diffusion osmotic pressures, is the achievement of a substantially uniform diffusion rate of the drug across the membrane over the operating life of the device. While such operating life would depend primarily on the drug involved and the purpose of its administration, in general the term would fall within the range of about one week to several months or more.

The invention is further illustrated by the following examples:

EXAMPLE 1

A device for controlling estrus in dogs was constructed generally as shown in the drawings utilizing a tubular casing 11 having an outside diameter of 13 mm, a chamber diameter of 5 mm and a membrane of silicone rubber having a thickness of 1 mm. The membrane support member 17 included 5 apertures each having a diameter of 1 mm. The capsule when fully charged contains 0.8 ml of ethanol with 8760 micrograms (mcg) of mibolerone dissolved therein. Coil spring 21 developed an internal pressure of about 800 mm Hg.

EXAMPLE 2

Fifteen female dogs (beagles) were treated with mibolerone utilizing devices prepared as set forth in this application and as specified in Example 1. Each device was placed in the vaginal tract of an animal during the month preceding the time when, on the basis of calculations from prior records, the dog was expected to come into estrus. The capsules were left in place for periods ranging between 10 to 12 weeks. Capsules which were removed at 10 weeks had approximately 0.1 ml solution left, whereas those removed at 12 weeks generally had no drug solution remaining therein. All dogs treated remained out of estrus during the periods in which the capsules remained vaginally implanted.

While in the foregoing we have disclosed an embodiment of the invention in considerable detail for purposes of illustration, it will be understood by those skilled in the art that many of these details may be varied without departing from the spirit and scope of the invention.

We claim:

1. A positive pressure drug releasing device comprising an elongated casing having a tubular side wall defining a chamber; said casing being open at one end and having an end wall at the other end thereof; a diffusion membrane secured to said casing and extending across said open end; a plunger slidably disposed within said chamber for axial movement therein; a drug solution in said chamber between said plunger and said membrane; said drug solution being diffusable through said membrane and absorbable by the body wall of a cavity in which said device is implanted; and a compression spring interposed between said plunger and said end wall; said spring being in a state of compression for producing a substantially uniform positive pressure on said drug solution of a magnitude sufficient to render negligible the effects of back diffusion osmotic pressure when the device is in use.

2. The device of claim 1 in which said compression spring is a coil spring capable of expanding from a compressed state to an expanded state within said chamber during the term of administration of said drug solution; said spring exerting a substantially uniform force over such range of expansion to generate a positive pressure within said chamber in the range of about 400 to 1500 mm Hg.

3. The device of claim 2 in which said spring generates a positive pressure within said chamber within the range of about 600 to 1200 mm Hg.

4. The device of claims 1, 2, or 3 in which said diffusion membrane is formed of silicone rubber.

5. The device of claim 1 in which a membrane support member is secured to said casing external to said membrane to brace said membrane against outward movement in response to pressure of said solution generated by said spring; said support member having a plurality of apertures extending therethrough and parallel with the longitudinal axis of said device; said apertures being sufficiently large in size to have no substantial adverse effect on the drug-metering action of said diffusion membrane.

6. The device of claims 1, 2, or 3 in which a plurality of flexible fingers slope radially outwardly and axially away from the end of said casing remote from said diffusion membrane for assisting in retaining said device within the vaginal tract of a warm-blooded animal.

7. The device of claim 6 in which said casing has a protective sleeve extending thereabout, said fingers being formed integrally with said sleeve.

8. The device of claim 8 in which said sleeve and fingers are formed of flexible non-irritating polymeric material.

9. The device of claim 6 in which an extraction cord is secured to said end wall between said fingers and extends from said device in the general axial direction of said fingers to facilitate extraction of the device fr

* * * * *